United States Patent [19]

Child et al.

[11] Patent Number: 5,262,579
[45] Date of Patent: Nov. 16, 1993

[54] SEPARATION OF SULFOLANE FROM CONJUNCT POLYMERIC BYPRODUCTS

[75] Inventors: Jonathan E. Child, Sewell; Anagha A. Gupte, Marlton; Tomas R. Melli, Sewell, all of N.J.; Sergei Yurchak, Media, Pa.

[73] Assignee: Mobil Oil Corporation, Fairfax, Va.

[21] Appl. No.: 991,918

[22] Filed: Dec. 17, 1992

Related U.S. Application Data

[63] Continuation-in-part of Ser. No. 833,684, Feb. 11, 1992, Pat. No. 5,191,150.

[51] Int. Cl.$^5$ .............................. C07C 2/62; C07C 7/10
[52] U.S. Cl. ................................ 585/802; 585/723; 585/724; 585/857
[58] Field of Search ................. 585/723, 724, 802, 857

[56] References Cited

U.S. PATENT DOCUMENTS

| | | | |
|---|---|---|---|
| 3,795,712 | 3/1974 | Torck et al. | 585/724 |
| 4,014,953 | 3/1977 | Brown, Jr. | 585/724 |
| 4,058,575 | 11/1977 | Cahn et al. | 585/724 |
| 4,199,409 | 4/1980 | Skraka | 585/724 |
| 4,317,795 | 3/1982 | Makovec et al. | 422/62 |
| 4,663,026 | 5/1987 | Louie et al. | 585/723 |
| 5,191,150 | 3/1993 | Child et al. | 585/809 |

Primary Examiner—Asok Pal
Attorney, Agent, or Firm—Alexander McKillop; Dennis P. Santini; Robert B. Furr, Jr

[57] ABSTRACT

The present invention provides a method for separating sulfolane from a mixture containing conjunct polymers, sulfolane, and hydrofluoric acid comprising the sequential steps of:
(a) removing HF from said mixture to provide an intermediate stream containing less than about 30 weight percent HF;
(b) contacting said intermediate stream with water;
(c) contacting said intermediate stream with an aliphatic hydrocarbon co-solvent having from about 3 to about 20 carbon atoms concurrently with said water-contacting step (b);
(d) recovering an extract stream enriched in sulfolane and hydrofluoric acid; and
(e) recovering a raffinate stream enriched in conjunct polymers.

12 Claims, 3 Drawing Sheets

SEPARATION OF SULFOLANE FROM CONJUNCT POLYMERIC BYPRODUCTS

CROSS REFERENCE TO RELATED APPLICATIONS

This is a continuation-in-part of application Ser. No. 07/833,684, filed Feb. 11, 1992, now U.S. Pat. No. 5,191,150.

FIELD OF THE INVENTION

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

U.S. Pat. No. 3,795,712 to Torck et al. relates to acid catalysts comprising a Lewis acid, a Bronsted acid, and a sulfone of the formula $R—SO_2—R'$, where R and R' are each separately a monovalent radical containing from 1 to 8 carbon atoms or form together a divalent radical having from 3 to 12 carbon atoms.

U.S. Pat. Nos. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

U.S application Ser. No. 07/719,879, filed Jun. 21, 1991, discloses an isoparaffin-olefin alkylation process which uses an HF/sulfolane catalyst containing relatively high concentrations of sulfolane, and is incorporated by reference for the details of isoparaffin-olefin alkylation with a sulfolane-enriched HF catalyst.

Allowed U.S. application Ser. No. 07/833,684, filed Feb. 11, 1992, discloses a method for separating a mixture of HF, sulfolane and conjunct polymeric byproducts formed during catalytic isoparaffin-olefin alkylation, and is in corporated by reference as if set forth at length herein.

HF-catalyzed isoparaffin-olefin alkylation forms a complex mixture of conjunct polymeric byproducts. These byproducts (commonly referred to as acid soluble oil or ASO) comprise polymers having differing degrees of conjugation which still further complicates the problem of separating ASO from a mixture of HF, sulfolane, and ASO.

SUMMARY OF THE INVENTION

The present invention provides a method for separating conjunct polymers and sulfolane from a mixture containing conjunct polymers, sulfolane, and hydrofluoric acid. In a first embodiment, the invention comprises the sequential steps of:

(a) removing HF from said mixture to provide an intermediate stream containing less than about 30 weight percent HF;

(b) contacting said intermediate stream with water;

(c) contacting said intermediate stream with an aliphatic hydrocarbon co-solvent having from about 3 to about 20 carbon atoms concurrently with said water-contacting step (b);

(d) recovering an extract stream enriched in sulfolane and hydrofluoric acid; and (e) recovering a raffinate stream enriched in conjunct polymers.

The method of the invention improves partitioning between the extract (sulfolane and water) phase and the raffinate (ASO) phase. Co-solvents useful in the present invention include aliphatic hydrocarbons, preferably those aliphatic hydrocarbons which remain in the liquid state under extraction conditions. Examples of particularly useful co-solvents include the normal and branched paraffins such as isobutane, isopentane, and the alkylate product formed by reacting isobutane with 2-butene.

Thus the invention decreases both capital and operating costs by decreasing both the size and the energy input requirements for the liquid/liquid extraction process equipment. Further, the method of the invention substantially decouples the upstream HF stripping operations from the extraction/gravitational separation step by decreasing feed sensitivity in the extraction/gravitational separation step. In other words, the method can effectively process a broader range of HF/sulfolane/ASO mixtures than was previously possible. By generating higher purity sulfolane and ASO streams, the method of the invention produces less hazardous waste material for treatment and disposal. Finally, the method decreases the viscosity of the ASO, thus permitting operation in a wider variety of process equipment.

Water extraction without the co-solvent of the invention leaves fractions of the conjugated ASO in the extract phase. But adding a co-solvent together with the water extractant improves partitioning, shifting the more conjugated fraction of the ASO into the raffinate phase (which is rich in ASO and hydrocarbon) and avoids accumulating ASO in the circulating catalyst.

The method finds particular utility in separating conjunct polymers from an HF/sulfolane catalyst used in an isoparaffin-olefin alkylation process. The hydrofluoric acid concentration of the mixture is preferably decreased by stripping prior to charging the HF/sulfolane/ASO mixture to the extraction/gravitational separation step. While any suitable inert stripping fluid may be employed in this initial stripping step, an isoparaffin is preferred, and an isoparaffin suitable for isoparaffin-olefin alkylation such as isobutane is still more preferred. Two sequential stripping steps may be used prior to the extraction/gravitational separation step, but the method generally operates effectively with only one stripping step prior to the extraction/gravitational separation step. If two-stage stripping is used, a second insert stripping fluid such as nitrogen is preferred. The stripped HF/sulfolane/ASO mixture preferably contains less than about 30 weight percent HF, preferably less than about 25 percent HF, and more preferably less than about 10 percent HF by weight.

The present process comprises the sequential steps of stripping and solvent extraction with both water and a paraffinic co-solvent to purify and recover sulfolane for recycle to the alkylation process unit. After the HF/sulfolane/water mixture is stripped to 30 weight percent or less of HF, the stripped mixture contacts water and the paraffinic co-solvent to extract sulfolane. The order of mixing with the paraffinic co-solvent and the water does not appear to be critical, but it is critical that the mixture first be at least partially stripped of HF, and that the gravitational separation step follow the extraction step. The terms "co-solvent" and "countersolvent" are used herein as synonyms referring to the hydrocarbon solvent of the invention.

In the gravitational extraction step, solids, sludge, and high density organics are drawn off as the most dense bottom layer, but, because the volume of this phase is typically quite small in comparison with the other two phases, the gravitational separation zone can be effectively operated as a two-phase gravitational separation with a bottom solids draw-off. The upper (less dense) liquid phase formed in the gravitational separation step is enriched in conjunct polyeric byproducts (acid soluble oil or ASO) and may be processed to recover residual sulfolane or may be processed for disposal, depending upon the concentration of recoverable residual sulfolane.

The lower (more dense) liquid phase withdrawn from the gravitational separation step (which contains HF, sulfolane, and water, and which is enriched in sulfolane) is then charged to a second stripping tower where HF is stripped from the sulfolane mixture. The stripping fluid in the second stripping tower may be any suitable fluid, although a light hydrocarbon suitable as a feedstock in the associated alkylation unit is preferred, and isobutane is particularly preferred.

The water dosage in the extraction step must be sufficient to provide the necessary mass transfer between the water and the feed, and typically falls within the range of from about 0.1 to about 2 mass units of solvent per mass unit of feed.

The extraction zone for contacting the HF/sulfolane/ASO mixture with water and the paraffinic co-solvent may comprise from about 1 to about 50 theoretical stages, preferably from about 1 to about 25 theoretical stages, and more preferably from about 1 to about 10 theoretical stages.

The extraction step may be carried out in any suitable apparatus, for example, one or more static mixers with downstream settlers, a tower containing perforate trays and/or at least one packed bed containing contact materials such as Berl saddles, Raschig rings, or the like. In the absence of the paraffinic co-solvent, the choice of process equipment is typically limited to static mixers with downstream settlers due to the density difference betweeen the HF/sulfolane/water mixture and the ASO.

EMBODIMENTS

Figure 1:
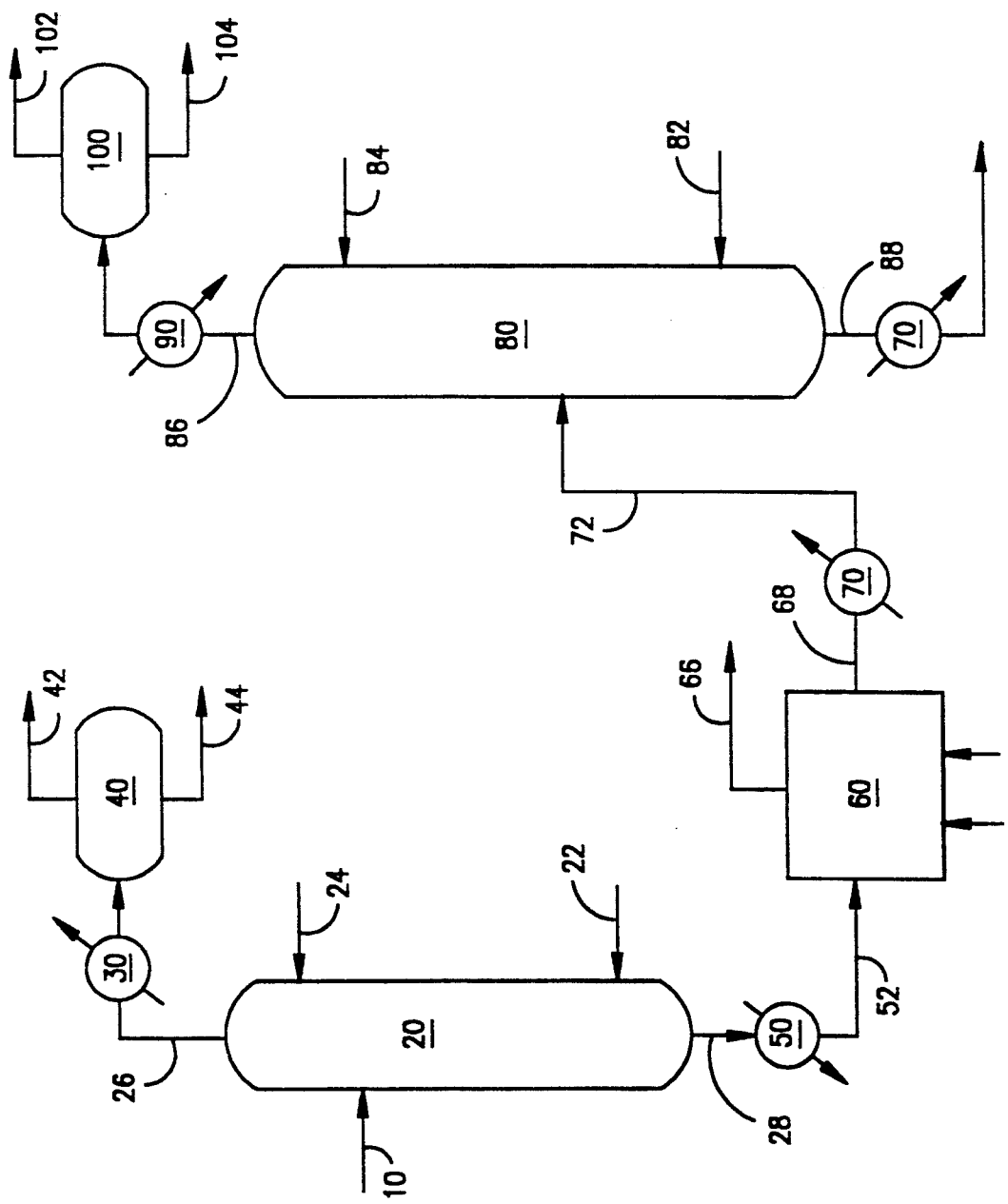
FIG. 1 is a simplified schematic diagram showing major processing steps in the method of the invention.

Referring now to FIG. 1, a slipstream of spent alkylation catalyst 10 flows from an operating HF/sulfolane catalyzed isoparaffin-olefin alkylation process unit (not shown) and enters primary distillation/stripping tower 20. Stripping gas, for example, isobutane, enters distillation/stripping tower 20 through line 22, carries stripped HF upwardly through the tower, and exits the primary distillation/stripping tower 20 via overhead line 26, flowing to overhead cooler 30 and accumulator 40. The HF/isobutane mixture condenses in accumulator 40 to form an HF-enriched stream and an isobutane-enriched stream. The HF-enriched stream may be recycled via line 42 directly back to the isoparaffin-olefin alkylation process unit (not shown). While the isobutane-enriched stream may also be optionally recycled to the alkylation process unit (not shown) via line 44, this stream is preferably charged to a lower section of the secondary distillation/stripping tower 80 via line 82 (described in greater detail below).

Figure 2:
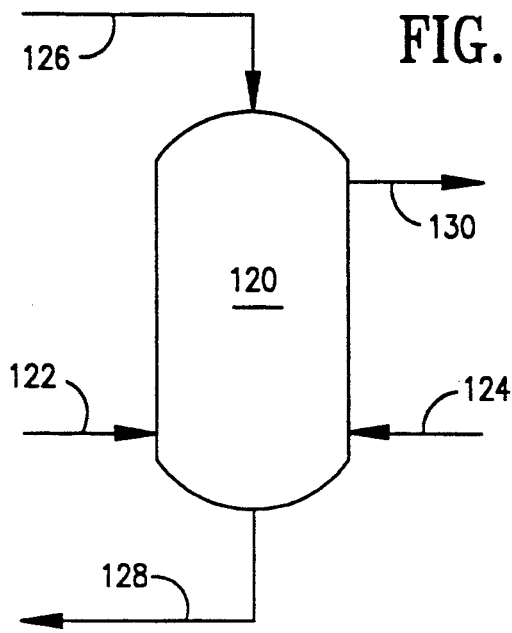
FIG. 2 is a simplified schematic diagram showing a first embodiment of the extraction step of the invention.
Figure 3:
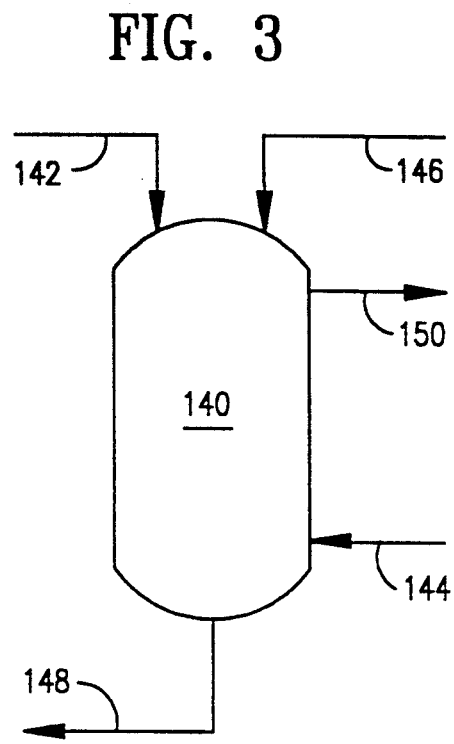
FIG. 3 is a simplified schematic diagram showing a second embodiment of the extraction step of the invention.
Figure 4:
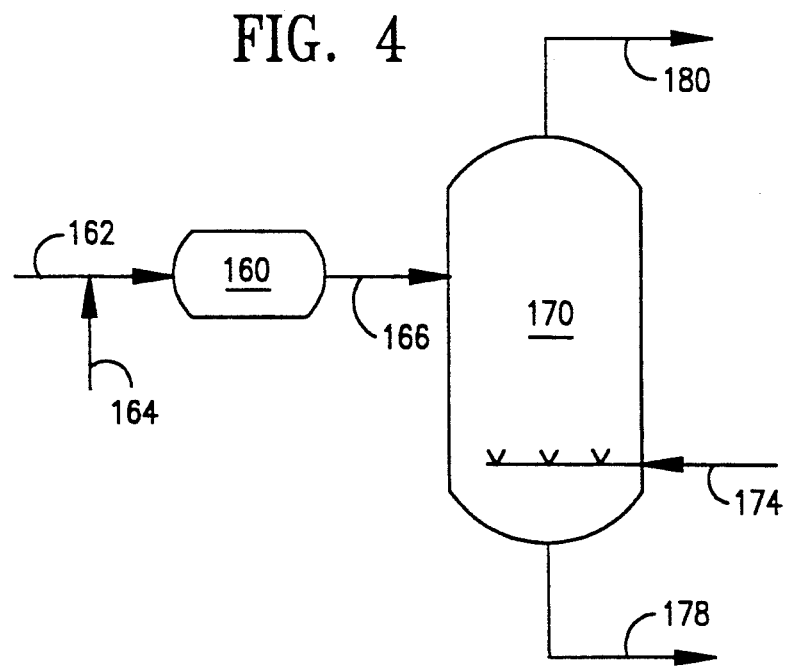
FIG. 4 is a simplified schematic diagram showing a second embodiment of the extraction step of the invention.
Figure 5:
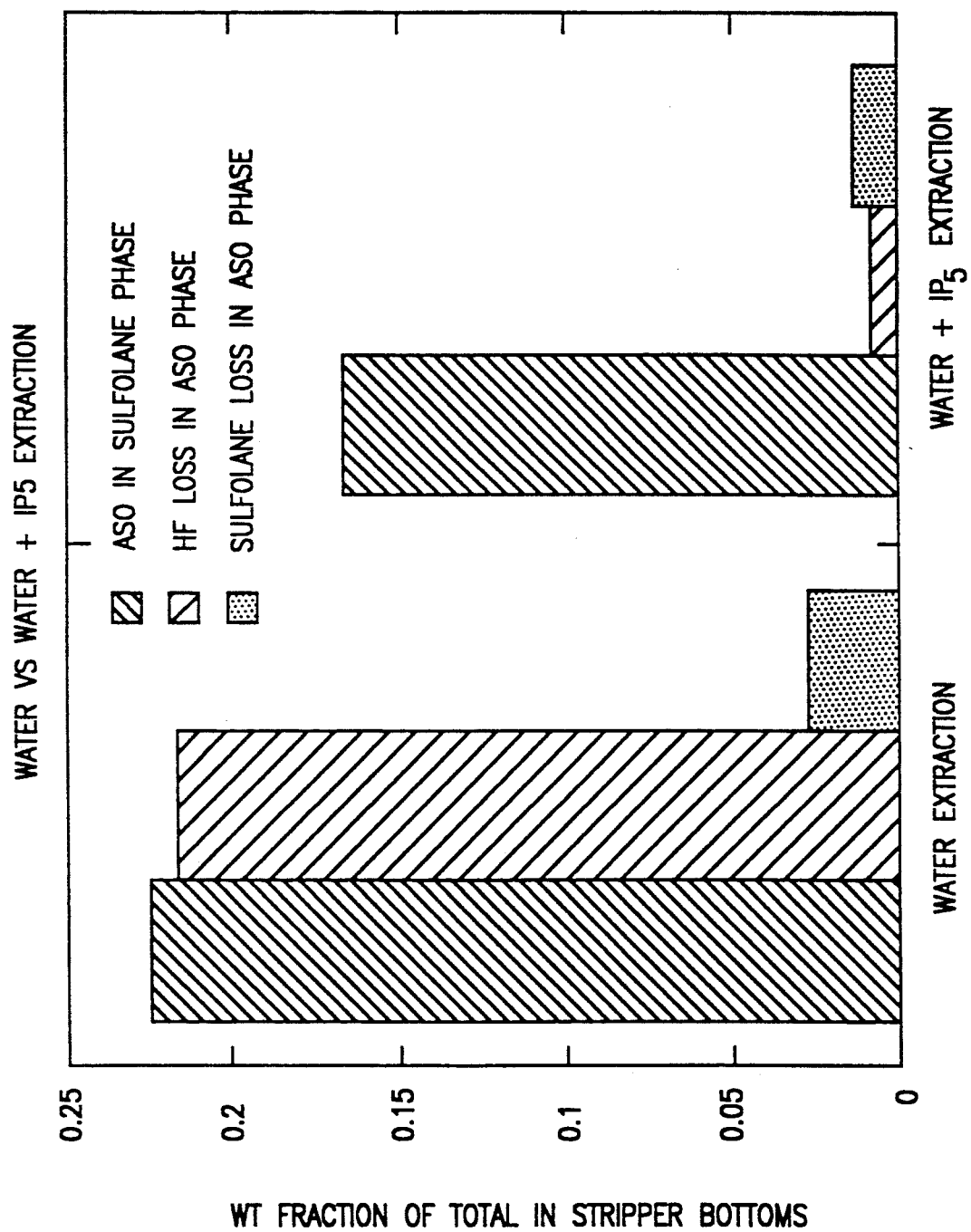
FIG. 5 is a bar graph comparing the distribution of feed components in the raffinate and extract streams for water extraction of sulfolane with and without a paraffinic co-solvent.

The bottoms product withdrawn from the primary distillation/stripping tower is charged through line 28 at tower temperature of about 300° F. and flows to cooler 50. The bottoms product, cooled to about 70° F., flows through line 52 and enters extractor/separator 60 at approximately the tower pressure of about 100 psig. Alternative embodiments for extractor/separator 60 are shown in FIGS. 2, 3, and 4, and are described in greater detail below. FIG. 1 shows one embodiment of a useful extractor/separator which comprises a settling tank with water charge line 62 and isobutane charge line 64 near the bottom of the tank. The ASO-enriched raffinate stream flows out of extractor/separator 60 via line 66, while the extract stream, enriched in sulfolane, water, and HF, flows from extractor/separator 60 through line 68 to cooler 70. Stripping follows the extraction step, and the extract stream flows from cooler 70 to the secondary distillation/stripping column 80 via line 72.

Isobutane (preferably from primary distillation/stripping column 20 via line 44) is heated to the desired temperature and enters secondary distillation/stripping column 80 through line 82 below the extract stream feed point and flows upwardly through the tower, becoming enriched in water and HF. Isobutane enriched in water and HF is withdrawn from secondary distillation/stripping column 80 through line 86, is at least partially condensed in overhead condenser 90, and then enters overhead accumulator 100. Isobutane flows overhead from overhead condenser 100 through line 102 and may be recycled to the alkylation process unit as feedstock. Water and unrecovered HF are drawn off the overhead accumulator 100 via line 104 for neutralization and disposal. Because the secondary distillation/stripping column operates at about 250° F. and 80 psig, the sulfolane-enriched bottoms product (withdrawn through line 88) must be cooled (in process cooler 110) before it is recycled to the alkylation reaction zone in the alkylation process unit.

FIGS. 2, 3, and 4 detail three alternative embodiments of extractor/settler process configurations useful in the present invention. Referring now to FIG. 2, the stripped HF/sulfolane/ASO mixture enters extractor/settler 120 near the bottom through line 122. Isobutane (the co-solvent) also enters extractor/settler 120 near the bottom through line 124, and may optionally be sparged through the liquid in the extractor/settler. Water (the extraction solvent) enters extractor/settler 120 through line 126, becomes enriched in sulfolane as it flows downwardly through the extractor/settler, and is withdrawn as the extract stream through line 128. The ASO-enriched raffinate stream flows out of extractor/settler 120 through line 130.

FIG. 3 shows a alternative embodiment in which both water (line 142) and the HF/sulfolane/ASO mixture (line 146) enter extractor/settler 140 near the top. Isobutane (the co-solvent) enters extractor/settler 140 near the bottom through line 144, and (as in the embodiment described with reference to FIG. 2, above) may optionally be sparged through the liquid in the extractor/settler. The downwardly-flowing water becomes enriched in sulfolane and is withdrawn from the extractor/settler through line 148. The ASO-enriched raffinate stream flows out of extractor/settler 140 through line 150.

FIG. 4 shows a third alternative embodiment which premixes the HF/sulfolane/ASO mixture before charging the mixture to a settler. The HF/sulfolane/water mixture (line 162) premixes with isobutane flowing through line 164 and the combined stream is charged to static mixer 160. Effluent from static mixer 160 flows through line 166 to extractor/settler 170, which may optionally be equipped with an isobutane sparger 174 to increase the co-solvent concentration in the extractor/settler. The sulfolane-enriched extract stream flows from extractor/settler 170 through line 178 while the ASO-enriched raffinate is withdrawn via line 180.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLE 2-4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid separate more readily into immiscible layers than the stripped mixtures containing higher HF concentrations.

EXAMPLE 5

The HF/sulfolane sample of Example 5 has the following composition:

| HF | 62 wt. % |
|---|---|
| Sulfolane | 27 wt. % |
| Isobutane | 4 wt. % |
| Water | 1-2 wt. % |
| ASO | 3 wt. % |

Balance to 100% other hydrocarbons. This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases. In Example 5, the two phases appear within several minutes of the HF concentration reaching about 2 wt. %.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

EXAMPLE 6

Stripped catalyst containing:

| HF | 9.3 wt. % |
|---|---|
| Sulfolane | 72 wt. % |
| ASO | 18.7 wt. % | is contacted with water at a water:catalyst ratio=0.5. Analysis of the extract and raffinate shows that 23% of the ASO is still in the extract sulfolane phase. Moreover, 22% of the HF and 3% of the sulfolane is lost in the ASO raffinate phase. However, when isopentane is utilized as a countersolvent during the extraction, the percentage of total AS in the sulfolane extract phase surprisingly drops to 17%. More dramatically, the HF loss in the ASO phase drops to 0.6% and the sulfolane loss in the ASO drops to 1.8%.

EXAMPLE 7

Spent catalyst from the alkylation reactor of an HF-catalyzed isoparaffin-olefin alkylation process containing:

| HF | 65 wt. % |
|---|---|
| Sulfolane | 30 wt. % |
| ASO | 3 wt. % |
| Water | 2 wt. % | is stripped to an HF concentration of less than 30 wt. % and subjected to phase separation, water extrction (water: catalyst ratio=0.5) and water extraction (water:-catalyst ratio=0.5) in the presence of isopentane as a countersolvent. A comparison of the efficiency of separation by the three processes is given below.

| | wt. % HF in stripper bottoms | wt. % ASO in sulfolane | wt. % sulfolane in ASO | wt. % ASO Removed |
|---|---|---|---|---|
| Phase Separation | 0 15 | 2.2 25.2 | 11.9 — | 85.6 |
| Water Extraction Only | 22.7 | 3.05 | 10.4 | 88.9 |
| Water Extraction with Isopentane Countersolvent | 22.7 | 0.78 | 0.66 | 96.7 |

Even at 22.7% HF in the stripped catalyst, using isopentane as a backwash countersolvent improves removal of ASO from sulfolane rich phase into raffinate and dramatically lowers sulfolane losses in ASO. Moreover, UV spectral analysis shows that use of isopentane results in removal of ASO species that could not be extracted by water.

EXAMPLES 8 and 9

Examples 8 and 9 compare the performance of two embodiments of the present process. Example 8 shows operation of the process configuration of FIG. 4 while Example 9 shows operation of the configuration illustrated in FIG. 2.

EXAMPLE 8

Stripped catalyst (temp=70° F.) from the stripper tower bottoms containing:

| HF | 10 wt. % |
|---|---|
| Sulfolane | 78 wt. % |
| ASO | 10 wt. % |
| Water | 2 wt. % | together with water for extraction and an isobutane countersolvent is sent to a mixer settler configuration. After the water, catalyst and hydrocarbon are ultimately mixed in a static mixer and allowed to separate in a settler the one stage extraction process gives

| Extract | 0.5 wt. % ASO |
|---|---|
| | 38 wt. % water |
| | 54.4 wt. % sulfolane |
| | 7.1 wt. % HF |
| Raffinate | 16.5 wt. % ASO |
| | 83.5 wt. % isobutane. |

EXAMPLE 9

The isobutane as well as stripped catalyst enter through the bottom of a liquid/liquid extraction packed column with 5 stages. The water for extraction enters the column at the top. The extract and raffinate streams contain the following:

| Extract | 38.2 wt. % water |
|---|---|
| | 54.7 wt. % sulfolane |
| | 7.13 wt. % HF |
| Raffinate | 16.7 wt. % ASO |
| | 83.3 wt. % isobutane. |

All the ASO is separated from sulfolane using 5 stages in one packed column.

Changes and modifications in the specifically described embodiments can be carried out without departing from the scope of the invention which is intended to be limited only by the scope of the appended claims.

What is claimed is:

1. A method for separating sulfolane from a mixture containing conjunct polymers, sulfolane, and HF comprising the sequential steps of:
    (a) removing HF from said mixture to provide an intermediate stream containing less than about 30 weight percent HF;
    (b) contacting said intermediate stream with water;
    (c) contacting said intermediate stream with an aliphatic hydrocarbon co-solvent having from about 3 to about 20 carbon atoms concurrently with said water-contacting step (b);
    (d) recovering an extract stream enriched in sulfolane and hydrofluoric acid; and
    (e) recovering a raffinate stream enriched in conjunct polymers.

2. The method of claim 1 wherein said contacting step (c) further comprises countercurrently contacting said mixture with said paraffinic co-solvent.

3. The method of claim 1 wherein said conjunct polymers are formed as byproduct in an isoparaffin-olefin alkylation process.

4. The method of claim 1 wherein said HF removal step (a) further comprises stripping HF from said mixture with a stripping fluid.

5. The method of claim 4 wherein said stripping fluid comprises at least one selected from the group consisting of isoparaffins and normal paraffins.

6. The method of claim 4 wherein said stripping fluid comprises the alkylate product formed by reacting an isoparaffin with an olefin.

7. The method of claim 4 wherein said stripping fluid comprises at least one selected from the group consisting of normal butane and isobutane.

8. The method of claim 4 wherein said stripping step comprises sequentially stripping said mixture with isoparaffin and then stripping said mixture with nitrogen.

9. The method of claim 1 wherein said mixture contains less than about 25 percent hydrofluoric acid by weight.

10. The method of claim 9 wherein said mixture contains less than about 10 percent hydrofluoric acid by weight.

11. A method for separating sulfolane from a mixture containing conjunct polymers, sulfolane, and HF comprising the sequential steps of:
   (a) removing HF from said mixture to provide an intermediate stream containing less than about 30 weight percent HF;
   (b) contacting said intermediate stream with water; and
   (c) concurrently with said contacting step (b), contacting said intermediate stream with an aliphatic hydrocarbon co-solvent at a dosage sufficient to produce a sulfolane-enriched extract stream which is essentially free of conjunct polymer species which cannot be extracted by water in the absence of hydrocarbon co-solvent.

12. The method of claim 11 further comprising contacting said intermediate stream with said aliphatic co-solvent at a dosage sufficient to partition a major portion of conjugated conjunct polymers into a raffinate stream.

* * * * *